United States Patent [19]
Singh et al.

[11] Patent Number: 5,905,076
[45] Date of Patent: May 18, 1999

[54] 6-SUBSTITUTED AMINO-4-OXA-1-AZABICYCLO [3,2,0] HEPTAN-7-ONE DERIVATIVES AS CYSTEINE PROTEASE INHIBITORS

[75] Inventors: Rajeshwar Singh; Nian E. Zhou, both of Edmonton, Canada; Degi Guo, Phoenixville, Pa.; Alan Cameron, Montreal, Canada; Jadwiga Kaleta, Edmonton, Canada; Enrico Purisima, Pierrefonds, Canada; Robert Menard, St. -Laurent, Canada; Ronald George Micetich, Sher Pk., Canada

[73] Assignee: National Research Council of Canada, Ottawa, Canada

[21] Appl. No.: 08/831,250

[22] Filed: Apr. 8, 1997

Related U.S. Application Data

[60] Provisional application No. 60/015,288, Apr. 10, 1996.

[51] Int. Cl.$^6$ ........................ A61K 31/395; C07D 487/08
[52] U.S. Cl. ............................................ 514/210; 540/347
[58] Field of Search ............................ 540/347; 514/210

[56] References Cited

U.S. PATENT DOCUMENTS 4,202,819  5/1980  Kellett et al. ........................ 260/245.3

FOREIGN PATENT DOCUMENTS

| | | |
|---|---|---|
| 3427651 | 6/1985 | Germany . |
| WO 88/10266 | 12/1988 | WIPO . |
| WO 95/18807 | 7/1995 | WIPO . |
| WO 96/32408 | 10/1996 | WIPO . |

OTHER PUBLICATIONS

Mayer et al., Progress in clinical and biological research, (1989) 317, 809–818.
Saito et al., Proc. Natl. Acad. Sci. USA, vol. 90, pp. 2628–2632, Apr. 1993.
Otto et al., Chem Rev. 1997, 97, 133–171.
Wang et al., TiPS– Nov. 1994 (vol. 15), pp. 412–419.
Hara et al. Proc. Natl. Acad. Sci. USA, vol. 94, pp. 2007–2012, Mar. 1997.

*Primary Examiner*—Mukund J. Shah
*Assistant Examiner*—Bruck Kifle
*Attorney, Agent, or Firm*—Nikaido Marmelstein Murray & Oram LLP

[57] ABSTRACT

Novel 6-substituted amino-4-oxa-1-azabicyclo[3,2,0] heptan-7-one compounds, as well as the pharmaceutically acceptable salts thereof and diastereoisomers thereof, of formula I,

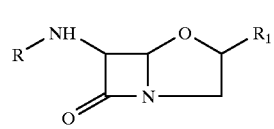

are disclosed, which exhibit excellent cysteine protease inhibitory activity and may be used for treatment of different diseases such as muscular dystrophy, arthritis, myocardial infarction, Alzheimer's disease, bacterial infection, common cold, osteroporosis and cancer metastasis.

11 Claims, No Drawings

6-SUBSTITUTED AMINO-4-OXA-1-AZABICYCLO [3,2,0] HEPTAN-7-ONE DERIVATIVES AS CYSTEINE PROTEASE INHIBITORS

This application claims the benefit of U.S. Provisional Application No. 60/015,288, filed Apr. 10, 1996.

BACKGROUND OF THE INVENTION

Cysteine proteases, such as cathepsins B, L, S, and $O_2$, have been implicated in a number of diseases, including cancer metastasis and invasion (Clin. Exp. Metastasis 1992, 10, 145–155; Cancer Metastasis Rev. 1990, 9, 333–352), arthritis (Int. J. Biochem. 1993, 25, 545–550; Arthritis Rheumatism 1994, 37, 236–247; J Rheumatol. 1993, 20, 1176–1183; Biochem. Pharmacol. 1993, 44, 1201–1207), muscular dystrophy (Am. J. Pathol. 1986, 122,193–198; 1987,127, 461–466), myocardial infarction (J. Am. Coll. Cardiol. 1983, 2, 681–688), bacterial infection (Rev. Infect. Dis., 1983, 5, 5914–5921) and common cold (Biochem. 1995, 34, 8172–8179). The calcium-associated cysteine proteases calpains I and II have been associated with ischemia and hypoxia, Alzheimer's disease (Proc. Natl. Acad. Sci. U.S.A. 1993, 90, 2628–2632) and cataracts (J. Biol. Chem. 1993, 268, 1937–1940). These medical disorders are thought to be due, among other factors, to the deregulation of the above mentioned cysteine proteases class of enzymes. Therefore this class of enzymes is excellent targets for the development of specific inhibitors as possible therapeutic agents.

Several types of cysteine proteases inhibitors have been reported, such as peptide aldehydes (Biochim. Biophys. Acta 1991, 1073–43), nitrites (Biochim. Biophys.Acta 1990, 1035, 62–70), halomethyl ketones (Anal. Biochem. 1985, 149, 461–465; Acta. Biol. Med. Ger. 1981, 40, 1503–1511; Biochem. Phar. 1992, 44, 1201–1207), diazomethyl ketones (Biochem. J. 1988, 253, 751), acyloxy methyl ketones (J. Med. Chem. 1994, 37, 1833–1840; J. Am. Chem. Soc. 1988,110, 4429–4431), ketomethylsulfonium salt (J. Biol. Chem. 1988, 263, 2768–2772), α-ketocarbonyl compounds (J. Med. Chem. 1993, 36, 3472–3480; 1994, 37, 2918–2929), vinyl sulfones (J. Med. Chem. 1995, 38, 3193–3196), monobactam derivatives (U.S. patent application Ser. No. 08/1415055, 1995) and epoxysuccinyl derivatives (Agric. Biol. Chem. 1978, 42, 523–527). These inhibitors, in general, have a peptidyl affinity group and a group reactive towards the thiol of the cysteine residue in cysteine proteases. Some of them are clinically useful. However, the efficacy in vivo is not as much as expected on the basis of in vitro inhibitory activity and may be due to lower selectivity towards other proteases and poor pharmacokinetics. There exists a continuing need to develop new cysteine proteases inhibitors with high selectivity, lower toxicity and better pharmacokinetics.

In continuation of our efforts to find out the low molecular weight cysteine protease inhibitors for therapeutic uses, we have focused our attention at 6-substituted oxapenam derivatives on the basis of the molecular modeling studies of 3-substituted-4-oxa-1-azabicyclo [3,2,0] heptan-7-one derivatives.

SUMMARY OF THE INVENTION

The present invention is based on the discovery that certain 6-substituted amino-4-oxa-1-azabicyclo[3,2,0] heptan-7-one derivatives exhibit excellent cysteine protease inhibitory activity which may be used for treatment of different diseases such as muscular dystrophy, arthritis, myocardial infarction, Alzheimer's disease, bacterial infection, common cold, osteroporosis or cancer metastasis.

Our laboratory has been actively involved in the search for novel types of cysteine proteases inhibitors with high selectivity among the cysteine protease class of enzymes. We have reported that 3-substituted-4-oxa-1-azabicyclo [3,2,0]heptan-7-one derivatives exhibited good cysteine protease inhibitory activity. Further to optimize and enhance the activity, we studied the interaction of inhibitors with the papain and cathepsin B enzyme crystal structures. Molecular modeling studies suggested that the 1-N atom in 4-oxa-1-azabicyclo[3,2,0]heptan-7-one ring can be involved in hydrogen-bonding to a protonated Histidine in the active site of cysteine proteases. This binding may weaken the lactamic bond and activate the four membered ring towards acylation of the thiol of the cysteine residue in cysteine proteases. A comparison of a model of a substrate (Cbz (benzyloxycarbonyl)-Phe-Ala-Nme (NH-methyl)) and that of the 4-oxa-1-azabicyclo[3,2,0]heptan-7-one ring in a tetrahedral intermediate complex with papain showed good superposition. We have also found that the substitution at position-6 of 4-oxa-1-azabicyclo[3,2,0] heptan-7-one will enhance the S2 subsite interaction with the papain enzyme. On the basis of this assumption, we have designed, synthesized and evaluated the cysteine protease inhibitory activity of various 6-substituted oxapenam and the finding is reported in the present invention.

In accordance to the present invention, there is provided 6-substituted amino-4-oxa-1-azabicyclo[3,2,0]heptan-7-one derivatives of general formula I or pharmaceutically acceptable salts thereof,

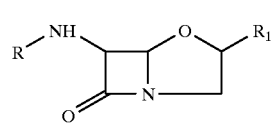

I wherein:

R is a 1–2 amino acid residue wherein the amine thereof is unsubstituted or substituted with group $R_2$, $R_1$ is (i) C1–C6 alkyl which is unsubstituted or substituted by 1–2 substituents independently selected from the group consisting of hydroxy, halogen, cyano, amino, heterocycle and phenyl, wherein the phenyl is unsubstituted or substituted by 1–2 substituents independently selected from hydroxy, halogen, cyano, carboxy or amino, (ii) phenyl which is unsubstituted or substituted by 1–2 substituents independently selected from hydroxy, halogen, cyano, carboxy, amino or phenyl, wherein the phenyl is unsubstituted or substituted by 1–2 substituents independently selected from hydroxy, halogen, cyano, carboxy or amino, (iii) C1–C6 alkoxy which is unsubstituted or substituted by 1–2 substituents independently selected from the group consisting of hydroxy, halogen, cyano, amino, heterocycle and phenyl, wherein the phenyl is unsubstituted or substituted by 1–2 substituents independently selected from hydroxy, halogen, cyano, carboxy or amino, or (iv) trifluoromethyl; and $R_2$ is selected from the group consisting of hydrogen, —$COOR_3$, —$COR_4$ and —$SO_2R_5$, wherein $R_3$ is C1–C6 alkyl which is unsubstituted or substituted with phenyl or heterocycle, $R_4$ is selected from the group consisting of (i) C1–C6 alkyl which is unsubstituted or substituted by 1–2 substituents independently selected from the group consisting of hydroxy, halogen, cyano, amino, heterocycle and phenyl, wherein the phenyl is unsubstituted or substituted by 1–2 substituents independently selected from hydroxy, halogen, cyano, carboxy or amino, (ii) C2–C4 alkenyl which is unsubstituted or substituted with heterocycle or phenyl, wherein the phenyl is unsubstituted or substituted by 1–2 substituents independently selected from hydroxy, halogen, cyano, amino or carboxy, (iii) C2–C4 alkynyl, (iv) C3–C6 cycloalkyl, (v) a phenyl group which is unsubstituted or substituted by 1–3 substituents independently selected from the group consisting of hydroxy, halogen, carboxy, cyano, amino, trifluoromethyl and phenyl group which is unsubstituted or substituted by 1–3 substituents independently selected from the group consisting of hydroxy, halogen, carboxy, cyano, amino and trifluoromethyl, and (vi) a heterocycle which may be mono or bicyclic having 1–3 heteroatoms independently selected from N, S and O, and $R_5$ is selected from the group consisting of (i) C1–C6 alkyl, (ii) alkenyl which is unsubstituted or substituted with heterocycle or phenyl, (iii) phenyl which is unsubstituted or substituted by 1–3 substituents independently selected from the group consisting of hydroxy, halogen, carboxy, cyano, amino, C1–C4 alkyl group, C1–C2 alkoxy group, trifluoromethyl and phenyl which is unsubstituted or substituted by 1–3 substituents independently selected from the group consisting of hydroxy, halogen, carboxy, cyano, amino, C1–C4 alkyl group, C1–C2 alkoxy group and trifluoromethyl, and (iv) naphthyl which is unsubstituted or substituted by 1–3 substituents independently selected from the group consisting of hydroxy, halogen, cyano, carboxy, amino, C1–C4 alkyl group, C1–C2 alkoxy group, trifluoromethyl and phenyl which is unsubstituted or substituted by 1–3 substituents independently selected from the group consisting of hydroxy, halogen, carboxy, cyano, amino, C1–C4 alkyl group, C1–C2 alkoxy group and trifluoromethyl.

The pharmaceutically acceptable salts of formula I are preferably selected from sodium, potassium, magnesium, calcium, hydrogen chloride, tartaric acid, succinic acid, fumaric acid and p-toluenesulfonic acid salts.

The term "1–2 amino acid" used herein is one amino acid or one dipeptide consisting of two amino acids which are bound through a peptide bond. The term "1–2 amino acid" encompasses any of the "natural" amino acids and unnatural amino acids.

Examples of amino acids are α-amino acids which are the constituents of normal protein, or their optical isomers. Examples include glycine, D- or L-alanine, D- or L-valine, D- or L-leucine, D- or L-isoleucine, D- or L-serine, D- or L-threonine, D- or L-aspartic acid, D- or L-glutamic acid, D- or L-asparagine, D- or L-glutamine, D- or L-lysine, D- or L-arginine, D- or L-phenylalanine, D- or L-tyrosine, D- or L-methionine, D- or L-proline and the like. Unnatural amino acids include, for example, D- or L-phenylglycine, D- or L-homophenylalanine, D- or L-pyridylalanine, D- or L-thienylalanine, D- or L-naphthylalanine, D- or L-halophenylalanine, D- or L-cyclohexylalanine, tert-butyl glycine and the like.

The term "heterocycle", unless otherwise described, used herein includes mono-, bi-, or tricyclic 5–14 membered rings having 1–4 heteroatoms selected from N, S and O. Examples of heterocycles are 1,2,3-triazole, 1,2,4-triazole, imidazole, pyrrole, pyrazole, thiophene, pyrrolidine, pyridine, piperidine, pyrimidine, piperazine, morpholine, thiomorpholine, 1-quinoline, 2-quinoline, isoalloxazine, phenoxazine, phenothiazine, and the like.

The 4-oxa-1-azabicyclo[3,2,0]heptan-7-one nucleus carries two asymmetric carbon atoms at position 5 and 6, and can therefore exist as 4-diastereoisomers. In general, the preferred isomer is that in which the hydrogen atoms at C5 and C6 are trans to each other this isomer has superior inhibitory activity against different cysteine proteases such as Cathepsin B, and Cathepsin L. Such diasterioisomers and their racemic mixtures are also included as cysteine protease inhibitors of the present invention.

More specifically, the most preferred embodiments of the present invention include the following compounds:

(5R,6S)-6-(N-benzyloxycarbonyl-L-phenylalanyl)-amino-4-oxa-1-azabicyclo[3,2,0]heptan-7-one;

(5R,6S)-6-(N-benzyloxycarbonyl-L-pronyl)-amino-4-oxa-1-azabicyclo[3,2,0]heptan-7-one;

(5R,6S)-6-(N-benzyloxycarbonyl-L-isoleucyl)-amino-4-oxa-1-azabicyclo[3,2,0]heptan-7-one;

(5R,6S)-6-(N-benzyloxycarbonyl-L-alanyl)-amino-4-oxa-1-azabicyclo[3,2,0]heptan-7-one;

(5R,6S)-6-(N-benzyloxycarbonyl-L-leucyl)-amino-4-oxa-1-azabicyclo[3,2,0]heptan-7-one;

(5R,6S)-6-(N-benzyloxycarbonyl-phenylglycyl)-amino-4-oxa-1-azabicyclo[3,2,0]heptan-7-one;

(5S,6S)-6-(N-benzyloxycarbonyl-L-phenylalanyl)-amino-4-oxa-1-azabicyclo[3,2,0]heptan-7-one;

(5R,6S)-6-{N-(3-phenylpropionoyl}-L-phenylalanyl)amino-3-phenyl-4-oxa-1-azabicyclo[3,2,0]heptan-7-one; and (5S,6S)-6-{N-(3-phenylpropionoyl)-L-phenylalanyl}-amino-3-bromomethyl-4-oxa-1-azabicyclo[3,2,0]heptan-7-one.

Compounds of formula I may be utilized for treatment of different diseases, including muscular dystrophy, arthritis, myocardial infarction, Alzheimer's disease, bacterial infection, common cold, osteroporosis or cancer metastasis. Examples of cancer metastasis are breast, lung, liver, colon, brain and prostate cancers.

DESCRIPTION OF PREFERRED EMBODIMENTS

The present invention relates to the 6-substituted amino-4-oxa-1-azabicyclo[3,2,0]heptan-7-one derivatives having excellent cysteine protease inhibitory activity and selectivity among cysteine proteaess. The compounds of this invention are characterized by having a substitution at position 6 of 4-oxa-1-azabicyclo[3,2,0]heptan-7-one skeleton. The 6-substituted amino-4-oxa-1-azabicyclo[3,2,0]heptan-7-one derivatives were prepared by the general synthetic route as represented in scheme I.

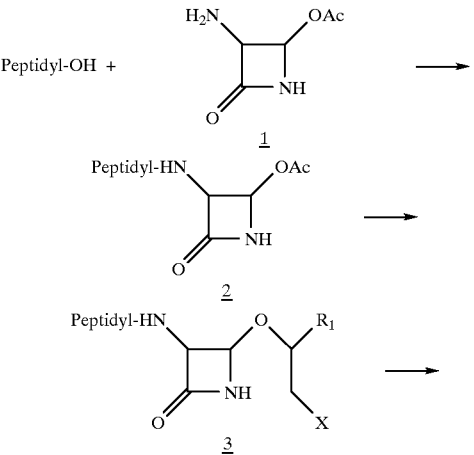

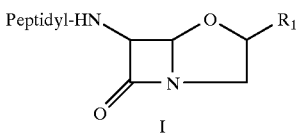

The derivatives of general formula I were prepared from the common intermediate 1. The preparation of compound I was carried out by the synthetic route as described in Eur. J. Med. Chem. 1992, 27, 131–140 starting from 6-aminopenicillanic acid. The peptidyl group is a 1–2 amino acid residue as defined above with a protective group at N-terminal. The intermediate 1 was coupled either with protected peptidyl carboxylic acid in the presence of 1,3-dicyclohexylcarbodiimide (DCC), or with acid chloride in the presence of base, or with anhydride in the presence of base or activated ester, to produce compound 2. Compound 3 was obtained by reacting of 2 with 2-substituted ethanol in the presence of lewis acids such as zinc acetate, zinc iodide, zinc chloride, titanium tetrachloride, palladium acetate, boron trifluoride, aluminium trichloride and the like, wherein X is a leaving group selected from a chlorine, bromine, iodine, methanesulfonyloxy or toluenesulfonyloxy group. Conversion of 3 to I was done by cyclization using a suitable base such as potassium carbonate, sodium carbonate, cesium carbonate in a non reactive solvent.

Alternatively, the derivatives of general formula I were also prepared by the general synthetic route as represented in scheme II

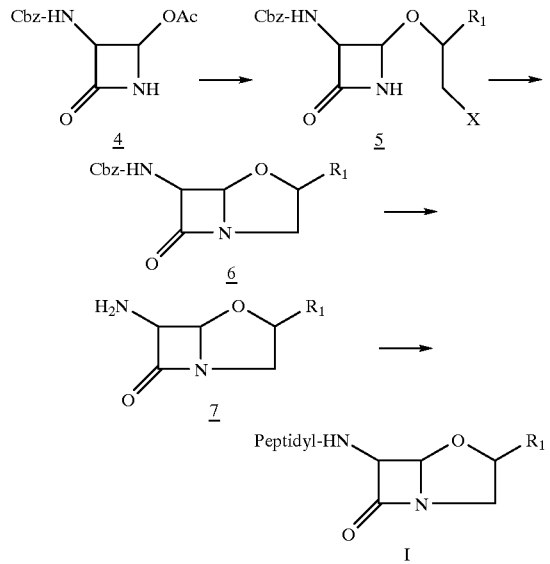

The intermediate 4 was reacted with 2-substituted ethanol in the presence of lewis acids such as zinc acetate, zinc iodide, zinc chloride, titanium tetrachloride, palladium acetate, boron trifluoride, aluminium trichloride and the like, wherein X is a leaving group selected from a chlorine, bromine, iodine, methanesulfonyloxy or toluenesulfonyloxy group to give compound 5. Cyclization of 5 using a suitable base such as potassium carbonate, sodium carbonate, cesium carbonate in a non reactive solvent gives 6-protected amino-4-oxa-1-azabicyclo[3,2,0]heptan-7-one 6. The benzyloxycarbonyl (denoted "Cbz") protected amino-4-oxa-1-azabicyclo[3,2,0]heptan-7-one 6 was deprotected by hydrogenation in the presence of a metal catalyst, such as Pd, Pt, or Rh, under normal pressure to high pressure to give compound 7. The derivatives of general formula I were obtained by reacting of amino-4-oxa-1-azabicyclo[3,2,0] heptan-7-one 7 with protected peptidyl carboxylic acid in the presence of DCC, or through acid chloride in the presence of base, or through anhydride in the presence of base or the activated ester.

In the above processes, the reactants are reacted together with solvent at elevated or low temperatures for sufficient time to allow the reaction to proceed to completion. The reaction conditions will depend upon the nature and reactivity of the reactants, and would be readily understood by those of skill in the art.

Wherever a base is used in a reaction, it is preferably selected from the group consisting of triethyl amine, pyridine, 4-dimethylaminopyridine, diisopropylamine, 1,5-diazabicyclo[4,3,0]non-5-ene, 1,8-diazabicyclo[5,4,0] undec-7-ene, sodium carbonate, potassium carbonate and cesium carbonate. Preferred solvents for the reaction are non reactive solvents. Depending on the reactants, a solvent will generally be selected from the group consisting of benzene, toluene, acetonitrile, tetrahydrofuran, ethanol, methanol, chloroform, ethyl acetate, methylene chloride, dimethyl formamide, dimethyl sulfoxide, hexamethyl phosphoric triamide, and the like. Solvent mixtures may also be utilized. Reaction temperatures generally range from between −70° C. to 150° C. The preferred molar ratio of reactants are 1:1 to 5. The reaction time range from 0.5 to 72 hours, depending on the reactants.

The compounds of this invention, when used alone or in combination with other drugs as an agent for treating muscular dystrophy, arthritis, myocardial infarction, Alzheimer's disease, bacterial infection, common cold, osteroporosis or cancer metastasis in mammals including humans, may take pharmaceutical dosage forms including parenteral preparation such as injections, suppositories, aerosols and the like, oral preparations such as tablets, coated tablets, powders, granules, capsules, liquids and the like, and topical preparations such as lotions, solutions, creams, ointments or dusting powders. Injections are generally preferred. The above preparations are formulated in a manner known in the art.

For the formulation of solid preparations for oral administration, an excipient, and if desired, a binder, disintegrator, lubricant, coloring agent, corrigent, flavor, etc. is added to the compound of the invention, and then tablets, coated tablets, granules, powders, capsules or the like are prepared in a conventional manner.

For the formulation of injections, a pH adjusting agent, buffer, stabilizer, isotonic agent, local anesthetic or the like is added to the active ingredient of the invention. Injections for subcutaneus, intramuscular or intravenous administration can be prepared in the conventional manner.

For the formulation of suppositories, a base, and, if desired, a surfactant are added to the active ingredient of the invention, and the suppositories are prepared in a conventional manner.

The excipients useful for solid preparations for oral administration are those generally used in the art, such as lactose, sucrose, sodium chloride, starches, calcium carbonate, kaolin, crystalline cellulose, methyl cellulose, glycerin, sodium alginate, gum arabic and the like. Other ingredients which may be used in the formulations of the invention include binders such as polyvinyl alcohol, polyvinyl ether, polyvinyl pyrrolidone, ethyl cellulose, gum arabic, shellac, sucrose, water, ethanol, propanol, carboxymethyl cellulose, potassium phosphate and the like; lubricants such as magnesium stearate, talc and the like; and additives such as usual known coloring agents, disintegrators and the like. Examples of bases useful for the formulation of suppositories are oleaginous bases such as cacao butter, polyethylene glycol, lanolin, fatty acid triglycerides, witepsol (trademark, Dynamite Nobel Co. Ltd.) and the like. Liquid preparations may be in the form of aqueous or oleaginous suspensions, solutions, syrups, elixirs and the like, which can be prepared by a conventional way using additives.

For the formulation of topical preparations, the active ingredient of the invention can be incorporated into a cream, for example, comprising an aqueous emulsion of polyethylene glycols or liquid paraffin. The active ingredient of the invention can also be incorporated into an ointment comprising a white wax or white soft paraffin base together with such stabilizers and preservatives as may be required. Stabilizers and preservatives for topical preparations are well known to those of skill in the art.

The amount of the compound of formula I of the invention to be incorporated into the pharmaceutical composition of the invention varies with the dosage form, solubility and chemical properties of the compound, administration route, administration scheme and the like. Preferable the amount is about 1 to 25 w/w% in the case of oral preparations, about 0.1 to 5 w/w% in the case of injections which are parenteral preparations, and about 1 to 10 w/w% in the case of topical preparations.

The dosage of the compound I of the invention is suitably determined depending on the individual cases taking symptoms, age and sex of the subject and the like into consideration. Usually the dosage in the case of oral administration is about 50 to 1500 mg per day for an adult in 2 to 4 divided doses, and the dosage in the case of injection, for example, by intravenous administration is 2.0 ml (about 1 to 100 mg) which is administratered once a day for adults wherein the injection may be diluted with physiological saline or glucose injection liquid if so desired, and slowly administered over at least 5 minutes. The dosage in case of suppositories is about 1 to 1000 mg which is administered once or twice a day at an interval of 6 to 12 hours wherein the suppostories are administered by insertion into the rectum. For topical administration, the dosage is about 1 to 2500 mg which is administered one to four times a day.

EXAMPLE 1

(5R,6S)-6-benzyloxycarbonylamino-4-oxa-1-azabicyclo[3.2.0]heptan-7-one

A mixture of (3S,4S)-3-benzyloxycarbonylamino-4-acetoxy-azetidin-2-one (11.76 g, 42.3 mmole) which prepared by the known method (Eur. J. Med. Chem. 1992, 27, 131–140), 2-bromoethanol (3 ml, 42.3 mmole), and zinc acetate dihydrate (9.28 g, 42.3 mmole) in a mixture of benzene (100 ml) and toluene (100 ml) was refluxed for 5 hrs using Dean-Stark water separator. After cooling, the reaction mixture was partitioned between ethyl acetate (800 ml), acetone (100 ml) and water (500 ml). The organic layer was washed with water, brine and dried over sodium sulfate. After removal of the solvent, the residue was purified by silica gel column chromatography using ethyl acetate-hexane (6:4) as eluent and 2.04 g of (3S,4R)-3-benzyloxycarbonylamino-4-bromoethoxy-azetidin-2-one was obtained as white solid (yield: 14%).

A mixture of (3S,4R)-3-benzyloxycarbonylamino-4-bromoethoxy-azetidin-2-one (2.04 g, 5.945 mmole) and powder $K_2CO_3$ (903 mg, 6.54 mmole) in DMSO (20 ml) was stirred at room temperature overnight and then diluted with ethyl acetate, washed with cold water, brine, and dried over sodium sulfate. After removal of the solvent, 1.43 g of the title compound was obtained.

Yield: 92% m.p.: 200° C. (dec.) FAB-MS: 263 (M+H$^+$), calcd for $C_{13}H_{14}N_2O_4$ 262 IR (KBr, cm$^{-1}$): 3295, 1782, 1711, 1652, 1513, 1440 $^1$H NMR (CDCl$_3$), d (ppm): 3.11 (1H, m), 3.81 (1H, m), 4.10 (2H, m), 5.12 (2H, s), 5.17 (1H, d, J=2.6), 5.29–5.38 (2H, m), 7.35 (5H, bs).

EXAMPLE 2

(5R,6S)-6-(N-benzyloxycarbonyl-L-phenylalanyl)-amino-4-oxa-1-azabicyclo[3.2.0]heptan-7-one (5R,6S)-6-benzyloxycarbonylamino-4-oxa-1-azabicyclo[3,2,0]heptan-7-one (950 mg, 3.624 mmole) was hydrogenated with 3 g of 10% palladium on activated carbon in ethyl acetate (80 ml) at 50 psi hydrogen pressure at room temperature for 6 hrs. after removal of catalyst by filtration, deprotected (5R,6S)-6-amino-4-oxa-1-azabicyclo[3,2,0]heptan-7-one in ethyl acetate was obtained.

To a solution of N-benzyloxycarbonyl-L-phenylalanine (867 mg, 2.90 mmole) and triethylamine (323 mg, 3.2 mmole) in dichloromethane (20 ml), ethyl chloroformate (315 mg, 2.90 mmole) was added at –15° C. The reaction mixture was stirred at –10 to 5° C. for 1.5 hrs. Then a precooled (~–15° C.) solution of (5R,6S)-6-amino-4-oxa-1-azabicyclo[3,2,0]heptan-7-one in ethyl acetate (see above) was added at –15° C. and the resulting mixture was stirred at room temperature for 10 hrs. After removal of solvent, the residue was dissolved in ethyl acetate, washed with water, brine and dried over sodium sulfate. After removal of solvent, the residue was purified by silica gel column chromatography using ethyl acetate-hexane (55:45) as eluent and 205 mg of the title compound was obtained as white solid.

Yield: 17% m.p.: 144–145° C. FAB-MS: 432 (M+Na$^+$), calcd for $C_{22}H_{23}N_3O_5$ 409 IR (KBr, cm$^{-1}$): 3280, 1780, 1608, 1647, 1526, 1219 $^1$H NMR (DMSO-d$_6$), d (ppm): 2.67–3.14 (3H, m), 3.72 (1H, m), 4.05 (2H, m), 4.39 (1H, m), 4.93 (2H, s), 5.23 (1H, d, J=2.8), 5.42 (1H, dd, J=2.8, 9.1), 7.20–7.35 (10H, m), 7.58 (1H, d, J=8.8), 8.67 (1H, d, J=9.1).

EXAMPLE 3

(5R,6S)-6-(N-benzyloxycarbonyl-L-prolyl)-amino-4-oxa-1-azabicyclo[3.2.0]heptan-7-one By using a similar method described in example 2, the title compound was obtained by reacting N-benzyloxycarbonyl-L-proline with (5R,6S)-6-amino-4-oxa-1-azabicyclo[3,2,0]heptan-7-one.

Yield: 5% FAB-MS: 360 (M+H$^+$), calcd for $C_{18}H_{21}N_3O_5$ 359 IR (KBr, cm$^{-1}$): 3295, 2930, 1694, 1653, 1522, 1409, 1346 $^1$H NMR (CDCl$_3$), d (ppm): 1.91–2.38 (4H, m), 3.53 (2H, bs), 3.81 (1H, m), 4.05 (2H, m), 4.37 (1H, bs), 5.16 (3H, m), 5.50 (1H, dd, J=2.8, 9.2), 6.50 (1H, bs), 7.35 (5H, bs).

EXAMPLE 4

(5R,6S)-6-(N-benzyloxycarbonyl-L-isoleucyl)-amino-4-oxa-1-azabicyclo[3.2.0]heptan-7-one By using a similar method described in example 2, the title compound was obtained by reacting N-benzyloxycarbonyl-L-isoleucine with (5R,6S)-6-amino-4-oxa-1-azabicyclo[3,2,0]heptan-7-one.

Yield: 5% m.p.: 100° C. (dec.) FAB-MS: 376 (M+H$^+$), calcd for C$_{19}$H$_{25}$N$_3$O$_5$ 375 IR (KBr, cm$^{-1}$): 3310, 2935, 1700, 1651, 1515, 1448 $^1$H NMR (CDCl$_3$), d (ppm): 0.86–0.97 (6H, m), 1.03–1.26 (2H, m), 1.47 (1H, m), 3.06–3.18 (1H, m), 3.74–3.86 (1H, m), 3.98–4.17 (3H, m), 5.10 (2H, s), 5.16 (1H, d, J=2.8), 5.32 (1H, d, J=9.6), 5.50 (1H, dd, J=2.8, 9.6), 6.49 (1H, d, J=9.1), 7.35 (5H, m).

EXAMPLE 5

(5R,6S)-6-(N-benzyloxycarbonyl-L-alanyl)-amino-4-oxa-1-azabicyclo[3.2,0]heptan-7-one (3S,4S)-3-benzyloxycarbonylamino-4-acetoxy-azetidin-2-one (2.00 g, 7.188 mmole) was hydrogenated with 2 g of 10% palladium on activated carbon in ethyl acetate (50 ml) at 50 psi hydrogen pressure at room temperature for 1.5 hrs. After removal of catalyst by filtration, the deproteced (3S, 4S)-3-amino-4-acetoxy-azetidin-2-one in ethyl acetate was obtained.

To a solution of N-benzyloxycarbonyl-L-alanine (1.604 g, 7.188 mmole) and triethylamine (799 mg, 7.91 mmole) in dichloromethane (30 ml), ethyl chloroformate (738 mg, 6.83 mmole) was added at −15° C. The reaction mixture was stirred at −10 to 5° C. for 1.5 hrs. Then a precooled (ca. −15° C.) solution of (3S,4S)-3-amino-4-acetoxy-azetidin-2-one in ethyl acetate (see above) was added at −15° C. and the resulting mixture was stirred at 0° C. to room temperature for 2 hrs. After removal of solvent, the residue was dissolved in ethyl acetate, washed with cold saturated NaHCO$_3$ solution, water, brine and dried over sodium sulfate. After removal of solvent, the residue was recrystallized from dichloromethane and (3S,4S)-3-(N-benzyloxycarbonyl-L-alanyl) amino-4-acetoxy-azetidin-2-one was obtained (1.36 g, 54% yield).

A mixture of (3S,4S)-3-(N-benzyloxycarbonyl-L-alanyl) amino-4-acetoxy-azetidin-2-one (1.36 g, 3.894 mmole), 2-bromoethanol (440 mg, 3.5 mmole), and zinc acetate dihydrate (642 mg, 2.9 mmole) in a mixture of benzene (40 ml) and toluene (40 ml) was refluxed for 5 hrs using Dean-Stark water separator. After cooling, the reaction mixture was partitioned between ethyl acetate (200 ml), acetone (25 ml) and water (150 ml). The organic layer was washed with water, brine and dried over sodium sulfate. After removal of the solvent, the residue was purified by silica gel column chromatography using ethyl acetate-hexane (2:1) as eluent and (3S,4R)-3-(N-benzyloxycarbonyl-L-alanyl) amino-4-bromoethoxy-azetidin-2-one was obtained (169 mg, 12% yield).

A mixture of (3S,4R)-3-(N-benzyloxycarbonyl-L-alanyl) amino-4-bromoethoxy-azetidin-2-one (159 mg, 0.384 mmole) and powder K$_2$CO$_3$ (58 mg, 0.42 mmole) in DMSO (2 ml) was stirred at room temperatute overnight and then diluted with ethyl acetate, washed with cold water, brine, and dried over sodium sulfate. After removal of the solvent, the residue was purified by silica gel column chromatography using ethyl acetate-hexane (3:1) as eluent and 49 mg of the title compound was obtained.

Yield: 38% m.p.: 150° C. (dec.) FAB-MS: 356 (M+Na$^+$), calcd for C$_{16}$H$_{19}$N$_3$O$_5$ 333 IR (KBr, cm$^{-1}$): 3285, 2950, 1701, 1679, 1645, 1527, 1444, 1325 $^1$H NMR (CDCl$_3$), d (ppm): 1.39 (3H, d, J=7.0), 3.12 (1H, m), 3.83 (1H, m), 4.08 (2H, m), 4.25 (1H, m), 5.11 (2H, s), 5.16 (1H, d, J=2.8), 5.20 (1H, bs), 5.49 (1H, dd, J=2.8, 9.3), 6.56 (1H, bs), 7.34 (5H, m).

EXAMPLE 6

(5R,6S)-6-(N-benzyloxycarbonyl-L-leucyl)-amino-4-oxa-1-azabicyclo[3.2,0]heptan-7-one By using a similar method described in example 5, the title compound was synthesized from (3S,4S)-3-benzyloxycarbonylamino-4-acetoxy-azetidin-2-one and N-benzyloxycarbonyl-L-leucine.

Yield: 1.5% (total yield for 3 steps) m.p.: 90° C. (dec.) FAB-MS: 398 (M+Na$^+$), calcd for C$_{19}$H$_{25}$N$_3$O$_5$ 375 IR (KBr, cm$^{-1}$): 3285, 1780, 1678, 1645, 1526, 1444, 1325 $^1$H NMR (DMSO-d$_6$), d (ppm): 0.86 (6H, m), 1.17–1.62 (3H, m), 3.05 (1H, m), 3.71 (1H, m), 4.06 (2H, m), 4.17 (1H, m), 5.02 (2H, s), 5.19 (1H, d, J=2.8), 5.35 (1H, dd, J=2.8, 9.0), 7.35 (5H, m), 7.44 (1H, d, J=8.5), 8.48 (1H, d, J=9.0).

EXAMPLE 7

(5R,6S)-6-(N-benzyloxycarbonyl-phenylglycyl)-amino-4-oxa-1-azabicyclo[3.2.0]heptan-7-one By using a similar method described in example 5, the title compound was synthesized from (3S,4S)-3-benzyloxycarbonylamino-4-acetoxy-azetidin-2-one and N-benzyloxycarbonyl-phenylglycine.

Yield: 0.7% (total yield for 3 steps) m.p.: 119–120° C. FAB-MS: 418 (M+Na$^+$), calcd for C$_{21}$H$_{21}$ N$_3$O$_5$ 395 IR (KBr, cm$^{-1}$): 3295, 2925, 1782, 1663, 1518 $^1$H NMR (CDCl$_3$), d (ppm): 3.10 (1H, m), 3.76 (1H, m), 4.04 (2H, m), 5.09 (2H, m), 5.16 (1H, d, J=2.8), 5.25 (1H, bs), 5.46 (1H, dd, J=2.9, 9.0), 5.96 (1H, bs), 6.22 (1H, d, J=9.0), 7.36 (10H, bs).

EXAMPLE 8

(5S,6S)-6-(N-benzyloxycarbonyl-L-phenylalanyl)-amino-4-oxa-1-azabicyclo[3.2.0]heptan-7-one (3S,4S)-3-benzyloxycarbonylamino-4-acetoxy-azetidin-2-one (6.00 g, 21.6 mmole) was hydrogenated with 6 g of 10% palladium on activated carbon in ethyl acetate (150 ml) at 50 psi hydrogen pressure at room temperature for 1.5 hrs. after removal of catalyst by filtration, the deproteced (3S, 4S)-3-amino-4-acetoxy-azetidin-2-one in ethyl acetate was obtained.

To a solution of N-benzyloxycarbonyl-L-phenylalanine (6.78 g, 22.6 mmole) and 1-hydroxybenzotriazole (3.05 g, 22.6 mmole) in tetrahydrofurane (150 ml), dicyclohexylcarbodiimide (4.45 g, 21.6 mmole) was added at 0° C. The reaction mixture was stirred at room temperature for 1.5 hrs and then cooled with an ice bath. The resulting N,N'-dicyclohexylurea was removed by filtration. Then a precooled (ca. −15° C.) solution of (3S,4S)-3-amino-4-acetoxy-azetidin-2-one in ethyl acetate (see above) was added at −15° C. and the resulting mixture was stirred at 0° C. to room temperature for 2 hrs. After removal of solvent, the residue was dissolved in ethyl acetate, washed with cold saturated NaHCO$_3$ solution, water, brine and dried over sodium sulfate. After removal of solvent, the residue was recrystallization from ethyl acetate-hexane and (3S,4S)-3-(N-benzyloxycarbonyl-L-phenylalanyl)amino-4-acetoxy-azetidin-2-one was obtained (4.57 g, 50% yield).

A mixture of (3S,4S)-3-(N-benzyloxycarbonyl-L-phenylalanyl)amino-4-acetoxy-azetidin-2-one (4.57 g, 10.8 mmole), 2-bromoethanol (1479 mg, 11.83 mmole), and zinc acetate dihydrate (1.78 g, 8.128 mmole) in a mixture of benzene (150 ml) and toluene (150 ml) was refluxed for 7 hrs using Dean-Stark water separator. After cooling, the reaction mixture was partitioned between ethyl acetate (1000 ml), acetone (100 ml) and water (500 ml). The organic layer was washed with water, brine and dried over sodium sulfate. After removal of the solvent, the residue was purified by silica gel column chromatography using ethyl acetate-hexane (55:45) as eluent and (3S,4S)-3-(N-benzyloxycarbonyl-L-phenylalanyl)amino-4-bromoethoxy-azetidin-2-one was obtained (650 mg, 12% yield).

A mixture of ($^3$S,4S)-3-(N-benzyloxycarbonyl-L-phenylalanyl)amino-4-bromoethoxy-azetidin-2-one (1.43 g, 2.918 mmole) and powder $K_2CO_3$ (444 mg, 3.2 mmole) in DMSO (20 ml) was stirred at room temperature overnight and then diluted with ethyl acetate, washed with cold water, brine, and dried over sodium sulfate. After removal of the solvent, the residue was recrystallized from ethyl acetate-hexane and 590 mg of the title compound was obtained.

Yield: 49% m.p.: 175–176° C. FAB-MS: 432 (M+Na$^+$), calcd for $C_{22}H_{23}N_3O_5$ 409 IR (KBr, cm$^{-1}$): 3285, 1779, 1683, 1659, 1525 $^1$H NMR (DMSO-d$_6$), d (ppm): 2.72–2.97 (3H, m), 3.76 (1H, m), 4.00 (2H, m), 4.23 (1H, m), 4.53 (1H, d, J=7.7), 4.96 (2H, d, J=2.3), 5.05 (1H, s), 7.27 (10H, bs), 7.62 (1H, d, J=8.5), 8.95 (1H, d, J=7.7).

EXAMPLE 9

(5R,6S)-6-{N-(3-phenylpropionoyl)-L-phenylalanyl}-amino-3-phenyl-4-oxa-1-azabicyclo [3,2.0]heptan-7-one A mixture of 1-phenyl-1,2-ethanediol (1.38 g, 10 mmole), immidazole (817 mg, 12 mmole), and tert-butylchlorodimethylsilane (1.81 g, 12 mmole) in DMF 15 (ml) was stirred at 0° C. for 1.5 hrs and then at room temperature overnight. The resulting mixture was diluted with ethyl acetate, washed with water, brine, and dried over sodium sulfate. After removal of the solvent, the residue was purified by silica gel column chromatography using ethyl acetate-hexane (1:4) as eluent. 2-(tert-butyidimethylsilyl)oxy-1-phenylethanol was obtained as an oil (2.6 g, 100% yield).

1H NMR (CDCl3), d (ppm): 0 (6H, s), 0.85 (9H, s), 2.92 (1H, d, J=2.1), 3.45–3.75 (2H, m), 4.60–4.75 (2H, m), 7.20–7.35 (5H).

(3S,4S)-3-benzyloxycarbonylamino-4-acetoxy-azetidin-2-one (5.56 g, 20 mmole) was hydrogenated with 5.6 g of 10% palladium on activated carbon in ethyl acetate (120 ml) at 50 psi hydrogen pressure at room temperature for 1.5 hrs. After removal of catalyst by filtration, the deproteced (3S, 4S)-3-amino-4-acetoxy-azetidin-2-one in ethyl acetate was obtained.

To a solution of N-(3-phenylpropionoyl)-L-phenylalanine (5.95 g, 20 mmole) and 1-hydroxybenzotriazole (2.7 g, 20 mmole) in tetrahydrofurane (150 ml), dicyclohexylcarbodiimide (4.12 g, 21.6 mmole)/THF (50 ml) was added at 0° C. The reaction mixture was stirred at room temperature for 1.5 hrs and then cooled with an ice bath. The resulting N,N'-dicyclohexylurea was removed by filtration. Then a pre-cooled (ca. −15° C.) solution of (3S,4S)-3-amino-4-acetoxy-azetidin-2-one in ethyl acetate (see above) was added at −15° C. and the resulting mixture was stirred at 0° C. to room temperature for 2 hrs. After removal of solvent, the residue was dissolved in ethyl acetate, washed with cold saturated $NaHCO_3$ solution, water, brine and dried over sodium sulfate. After removal of solvent, the residue was recrystallized from ethyl acetate and (3S,4S)-3-{N-(3-phenylpropionoyl)-L-phenylalanyl}amino-4-acetoxy-azetidin-2-one was obtained (7.2 g, 85% yield).

1H NMR (DMSO-d$_6$), d (ppm): 2.09 (3H, s), 2.36 (2H, m), 2.68 (2H, m), 2.75 (1H, dd, J=14, 10), 3.01 (1H, dd, J=14, 5), 4.53 (1H, m), 4.60 (1H, dd, J=8, 1), 5.75 (1H, d, J=1), 7.05–7.30 (1OH, m), 8.15 (1H, d, J=8), 8.72 (1H, d, J=8), 9.17 (1H, s).

A mixture of (3S,4S)-3-{N-(3-phenylpropionoyl)-L-phenylalanyl}amino-4-acetoxy-azetidin-2-one (4.36 g, 10.30 mmole), 2-(tert-butyldimethylsilyl)oxy-1-phenylethanol (2.6 g, 10.30 mmole), and zinc acetate dihydrate (2.26 g, 10.30 mmole) in a mixture of benzene (70 ml) and toluene (70 ml) was refluxed overnight using Dean-Stark water separator. After cooling, the reaction mixture was partitioned between ethyl acetate and water. The organic layer was washed with water, brine and dried over sodium sulfate. After removal of the solvent, the residue was purified by silica gel column chromatography using ethyl acetate-hexane (4:3) as eluent and (3S,4R)-3-{N-(3-phenylpropionoyl)-L-phenylalanyl}amino-4-{2-(tert-butyidimethylsilyl)oxy-1-phenyl ethoxy}-azetidin-2-one was obtained (440 mg, 7% yield).

$^1$H NMR (DMSO-d$_6$), d (ppm): 0 (6H, s), 0.83 (9H, s), 2.25–2.40 (2H, m), 2.65–3.10 (4H, m), 3.8–4.00 (2H, m), 4.45–4.55 (2H, m), 5.00–5.15 (2H, m), 7.00–7.40 (15H, m), 7.85 (1H, s), 8.30 (1H, m), 8.65 (1H, s).

A THF solution of 1 N BU$_4$NF (0.84 ml, 0.84 mmole) containing AcOH (35 mg, 0.56 mmole) was added to a solution of (3S,4R)-3-{N-(3-phenylpropionoyl)-L-phenylalanyl}amino-4-{2-(tert-butyldimethylsilyl)oxy-1-phenylethoxy}-azetidin-2-one (430 mg, 0.70 mmole) in THF (5 ml) at 0–5° C. The mixture was stirred at room temperature for 3 hrs, then poured into a silica gel column. The column was eluented with methanol-ethyl acetate (5:95) and 260 mg of (3S,4R)-3-{N-(3-phenylpropionoyl)-L-phenylalanyl}amino-4-(2-hydroxy-1-phenylethoxy)-azetidin-2-one was obtained (74% yield).

$^1$H NMR (DMSO-d$_6$), d (ppm): 2.30–2.45 (2H, m), 2.75–3.10 (4H, m), 3.75–4.10 (3H, m), 4.80–5.05 (2H, m), 6.40–6.70 (2H, m), 7.0–7.40 (15H, m), 7.61 (1H, bs), 7.95 (1H, d, J=8), 8.35 (1H, d, J=8).

p-Toluenesulfonyl chloride (119 mg, 0.62 mmol) was added to an ice-cooled solution of (3S,4R)-3-{N-(3-phenylpropionoyl)-L-phenylalanyl}amino-4-(2-hydroxy-1-phenyloxy)-azetidin-2-one (260 mg, 0.52 mmol) and pyridine (493 mg, 6.2 mmol) in dichloromethane (7 ml). The mixture was stirred at 0° C. for 2 hrs and then at room temperature overnight. After removal of solvent, the residue was purified by silica gel column chromatography using ethyl acetate-hexane (8:3) as eluent and 160 mg of (3S,4R)-3-{N-(3-phenylpropionoyl)-L-phenylalanyl}amino-4-{2-(p-toluenesulfonyl)oxy-1-phenylethoxy}-azetidin-2-one was obtained (47% yield).

$^1$H NMR (CDCl3), d (ppm): 2.30–2.45 (5H, m), 2.75–3.05 (4H, m), 4.20–4.40 (2H, m), 4.95–5.15 (2H, m), 6.40–6.60 (2H, m), 7.0–7.4 (18H, m), 7.75 (2H, dd, J=8.3, 3), 8.15 (1H, d, J=1.2), 8.55 (1H, d, J=7.6).

A mixture of (3S,4R)-3-{N-(3-phenylpropionoyl)-L-phenylalanyl}amino-4-{2-(p-toluenesulfonyl)oxy-1 -phenylethoxy}azetidin-2-one (160 mg, 0.244 mmol), lithium bromide (133 mg, 1.525 mmol) and HMPA (4 ml) was stirred at 60° C. for 1.5 hrs. The resulting mixture was diluted with ethyl acetate, washed with water, brine, and dried over sodium sulfate. After removal of solvent, the residue was purified by silica gel column chromatography using hexane-ethyl acetate (1:2) as eluent and 100 mg (3S,4R)-3-{N-(3-phenylpropionoyl)-L-phenylalanyl}-amino-4-(2-bromo-1-phenylethoxy)-azetidin-2-one as white foam was obtained in 72% yield.

A mixture of (3S,4R)-3-{N-(3-phenylpropionoyl)-L-phenylalanyl}amino-4-(2-bromo-1-phenylethoxy)-azetidin-2-one (100 mg, 0.177 mmole) and powder K$_2$CO$_3$ (27 mg, 0.195 mmole) in DMSO (3 ml) was stirred at room temperatute overnight and then diluted with ethyl acetate, washed with cold water, brine, and dried over sodium sulfate. After removal of the solvent, the residue was purified by silica gel column chromatography using hexane-ethyl acetate (1:2) as eluent, gave the title compound.

Yield: 30 mg (35%) m.p.: 132–135° C. IR (KBr, cm$^{-1}$): 3450, 3275, 1785, 1656, 1513, 1414, 1179, 693; $^1$H NMR (CDCl$_3$), d (ppm): 2.39(2H, m), 2.80–3.03(4H, m), 3.69(1H, d, J=6.1 Hz), 3.82(1H, d, J=61 Hz), 4.83(1H, d, J=3.5Hz), 5.15(1H, abq, J=8.8, 3.5), 5.11(1H, m), 6.17–6.43(1H, m), 7.01–7.57(15H, m), 8.22(1H,s), 8.44–8.66(1H, m)

EXAMPLE 10

(5S,6S)-6-{N-(3-phenylpropionoyl)-L-phenylalanyl}-amino-3-bromomethyl-4-oxa-1-azabicyclo[3.2.0]heptan-7-one A mixture of (3S,4S)-3-{N-(3-phenylpropionoyl)-L-phenylalanyl}amino-4-acetoxy-azetidin-2-one (1.67 g, 3.95 mmole), 1,3-dibromo-2-propanol (689 mg, 3.16 mmole), and zinc acetate dihydrate (435 mg, 1.98 mmole) in a mixture of benzene (25 ml) and toluene (25 ml) was refluxed overnight using Dean-Stark water separator. After cooling, the reaction mixture was partitioned between ethyl acetate (200 ml), acetone (40 ml) and water (150 ml). The organic layer was washed with water, brine and dried over sodium sulfate. After removal of the solvent, the residue was purified by silica gel column chromatography using ethyl acetate-hexane (4:3) as eluent and (3S,4S)-3-{N-(3-phenylpropionoyl)-L-phenylalanyl}amino-4-(1,3-dibromoprop-2-yl)oxy-azetidin-2-one was obtained (170 mg, 7% yield).

$^1$H NMR (CDCl3), d (ppm): 2.35–2.55 (2H, m), 2.75–3.10 (4H, m), 3.40–3.55 (4H, bs), 3.80–3.95 (1H, m), 4.39 (1H, d, J=7), 4.75–4.90 (1H, m), 5.09 (1H, s), 6.80 (1H, d, J=8), 7.0–7.30 (10H, m), 7.66 (1H, s), 7.83 (1H, d, J=7).

A mixture of (3S,4R)-3-{N-(3-phenylpropionoyl)-L-phenylalanyl}amino-4-(1,3-dibromoprop-2-yl)oxy-azetidin-2-one (170 mg, 0.29 mmole) and powder K$_2$CO$_3$ (44.5 mg, 0.322 mmole) in DMSO (3 ml) was stirred at room temperatute overnight and then diluted with ethyl acetate, washed with cold water, brine, and dried over sodium sulfate. After removal of the solvent, the residue was purified by silica gel preparative plate using hexane-ethyl acetate (1:2) as solvent for developing the plates. Out of 4 fractions, fraction 2 was obtained as title compound.

Yield: 20 mg (14%) m.p.: 150–152° C. IR (KBr, cm$^{-1}$): 3405, 1773, 1640, 1529, 1225; $^1$H NMR (DMSO-d$_6$), d (ppm): 2.46(2H, t), 2.85–3.00(6H, m), 3.35–3.44(2H, m), 4.06(1H, m), 4.43(2H, m), 4.77(1H, m), 5.23(1H, s), 6.32 (1H, d, J=8.1 Hz), 7.08–7.26(11H, m)

Testing of inhibitors for inhibition of Cathepsin B and L

Test Example 1

In vitro assay procedure for cathepsin B

The compounds of formula I were tested for inhibition of cathepsin B using the known method (A. J. Barret et al., Biochem. J. 1982, 201, 189–198). To a 170 μl of enzyme-buffer mixture (enzyme: r rat cathepsin B, diluted to give approximate 10 F units/min, buffer: 56 mM sodium acetate, 1.124 mM EDTA, 10 mM DTT, pH 5.1) a 10 μL of inhibitor (dissolved in DMSO) was added. After 10 min of incubation at room temperature, a 20 μl of 5 mM substrate (N-CBZ-Phe-Arg-AMC, dissolved in DMSO) was added to initiate reaction. Reading is followed up for 10 min at the fluoroscan reader (excitation at 380 nm emission at 460 nm).

A plot of percentage of inhibition vs inhibitor concentration is obtained, and IC$_{50}$ is determined using a linear regression calculations (concentration of inhibitor which will give 50% inhibition).

Test Example 2

In vitro assay procedure for cathepsin L

To a 170 μl of enzyme-buffer mixture (enzyme: r rat cathepsin L, diluted to give approximate 15 F units/min, buffer: 58.8 mM sodium citrate, 1.18 mM EDTA, 235 mM sodium chloride, 5 mM DTT, pH 5.0) a 10 μL of inhibitor (dissolved in DMSO) was added. After 10 min of incubation at room temperature, a 20 μl of 1 mM substrate (N-CBZ-Phe-Arg-AMC, dissolved in DMSO) was added to initiate reaction. Reading is followed up for 10 min at the fluoroscan reader (excitation at 380 nm emission at 460 nm).

A plot of percentage of inhibition vs inhibitor concentration is obtained, and IC$_{50}$ is determined using a linear regression calculations (concentration of inhibitor which will give 50% inhibition).

TABLE 1

In vitro inhibitory activity of compounds of formula I on cysteine proteases

| Example No. | IC$_{50}$ (μM) | |
| --- | --- | --- |
| | Cathepsin B | Cathepsin L |
| 1 | >50 | >50 |
| 2 | 4.56 | 0.26 |
| 3 | >50 | 9.40 |
| 4 | >50 | 9.88 |
| 5 | >50 | 38 |
| 6 | 30 | 0.60 |
| 7 | >50 | 1.83 |
| 8 | 12.2 | 0.004 |
| 9 | >50 | >50 |
| 10 | 1.91 | 0.016 |

We claim:
1. A 6-substituted amino-4-oxa-1-azabicyclo[3,2,0] heptan-7-one compound of formula I, or a pharmaceutically acceptable salt thereof or diastereoisomer thereof,

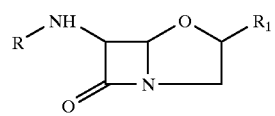

I wherein:
R is one alpha amino acid or one dipeptide consisting of two alpha amino acids which are bound through a peptide bond, wherein the amine thereof is unsubstituted or substituted with group R$_2$,
R$_1$ is selected from the group consisting of (i) C1–C6 alkyl which is unsubstituted or substituted by 1–2 substituents independently selected from the group consisting of hydroxy, halogen, cyano, amino, a mono-, bi-, or tricyclic 5–14 membered heterocyclic ring having 1–4 heteroatoms selected from N, S and O and phenyl, wherein the phenyl is unsubstituted or substituted by 1–2 substituents independently selected from hydroxy, halogen, cyano, carboxy and amino, (ii) phenyl which is unsubstituted or substituted by 1–2 substituents independently selected from hydroxy, halogen, cyano, carboxy, amino and phenyl which is unsubstituted or substituted by 1–2 substituents independently selected from hydroxy, halogen, cyano, carboxy and amino, (iii) C1–C6 alkoxy which is unsubstituted or substituted by 1–2 substituents independently selected from the group consisting of hydroxy, halogen, cyano, amino, a mono-, bi-, or tricyclic 5–14 membered heterocyclic ring having 1–4 heteroatoms selected from N, S and O and phenyl, wherein the phenyl is unsubstituted or substituted by 1–2 substituents independently selected from hydroxy, halogen, cyano, carboxy and amino, and (iv) trifluoromethyl; and $R_2$ is selected from the group consisting of hydrogen, —COOR$_3$, —COR$_4$ and —SO$_2$R$_5$, wherein $R_3$ is C1–C6 alkyl which is unsubstituted or substituted with phenyl or a mono-, bi-, or tricyclic 5–14 membered heterocyclic ring having 1–4 heteroatoms selected from N, S and O, $R_4$ is selected from the group consisting of (i) C1–C6 alkyl which is unsubstituted or substituted by 1–2 substituents independently selected from the group consisting of hydroxy, halogen, cyano, amino, a mono-, bi-, or tricyclic 5–14 membered heterocyclic ring having 1–4 heteroatoms selected from N, S and O and phenyl, wherein the phenyl is unsubstituted or substituted by 1–2 substituents independently selected from the group consisting of hydroxy, halogen, cyano, carboxy and amino, (ii) C2–C4 alkenyl which is unsubstituted or substituted with a mono-, bi-, or tricyclic 5–14 membered heterocyclic ring having 1–4 heteroatoms selected from N, S and O or phenyl, wherein the phenyl is unsubstituted or substituted by 1–2 substituents independently selected from the group consisting of hydroxy, halogen, cyano, amino and carboxy, (iii) C2–C4 alkynyl, (iv) C3–C6 cycloalkyl, (v) a phenyl group which is unsubstituted or substituted by 1–3 substituents independently selected from the group consisting of hydroxy, halogen, carboxy, cyano, amino, trifluoromethyl and phenyl group which is unsubstituted or substituted by 1–3 substituents independently selected from the group consisting of hydroxy, halogen, carboxy, cyano, amino and trifluoromethyl, and (vi) a heterocycle which may be mono or bicyclic having 1–3 heteroatoms independently selected from the group consisting of N, S and O, and $R_5$ is selected from the group consisting of (i) C1–C6 alkyl, (ii) alkenyl which is unsubstituted or substituted with a mono-, bi-, or tricyclic 5–14 membered heterocyclic ring having 1–4 heteroatoms selected from N, S and O or phenyl, (iii) phenyl which is unsubstituted or substituted by 1–3 substituents independently selected from the group consisting of hydroxy, halogen, carboxy, cyano, amino, C1–C4 alkyl group, C1–C2 alkoxy group, trifluoromethyl and phenyl which is unsubstituted or substituted by 1–3 substituents independently selected from the group consisting of hydroxy, halogen, carboxy, cyano, amino, C1–C4 alkyl group, C1–C2 alkoxy group and trifluoromethyl and (iv) naphthyl which is unsubstituted or substituted by 1–3 substituents independently selected from the group consisting of hydroxy, halogen, cyano, carboxy, amino, C1–C4 alkyl group, C1–C2 alkoxy group, trifluoromethyl and phenyl which is unsubstituted or substituted by 1–3 substituents independently selected from the group consisting of hydroxy, halogen, carboxy, cyano, amino, C1–C4 alkyl group, C1–C2 alkoxy group and trifluoromethyl.

2. The compound of claim 1, wherein the amino acids comprise natural amino acids.

3. The compound of claim 1, wherein the amino acids are selected from the group consisting of glycine, D- or L-alanine, D- or L-valine, D- or L-leucine, D- or L-isoleucine, D- or L-serine, D- or L-threonine, D- or L-aspartic acid, D- or L-glutamic acid, D-or L-asparagine, D- or L-glutamine, D- or L-lysine, D- or L-arginine, D- or L-phenylalanine, D- or L-phenylglycine, D- or L-tyrosine, D- or L-methionine and D- or L-proline.

4. The compound of claim 1, wherein the hydrogen atoms at the two asymmetric carbon atoms at positions 5 and 6 are trans to each other.

5. The compound of claim 1, wherein the compound is selected from the group consisting of:
(5R,6S)-6-(N-benzyloxycarbonyl-L-phenylalanyl)-amino-4-oxa-1-azabicyclo[3,2,0]heptan-7-one;
(5R,6S)-6-(N-benzyloxycarbonyl-L-prolyl)-amino-4-oxa-1-azabicyclo[3,2,0]heptan-7-one;
(5R,6S)-6-(N-benzyloxycarbonyl-L-isoleucyl)-amino-4-oxa-1-azabicyclo[3,2,0]heptan-7-one;
(5R,6S)-6-(N-benzyloxycarbonyl-L-alanyl)-amino-4-oxa-1-azabicyclo[3,2,0]heptan-7-one;
(5R,6S)-6-(N-benzyloxycarbonyl-L-leucyl)-amino-4-oxa-1-azabicyclo[3,2,0]heptan-7-one;
(5R,6S)-6-(N-benzyloxycarbonyl-phenylglycyl)-amino-4-oxa-1-azabicyclo[3,2,0]heptan-7-one;
(5S,6S)-6-(N-benzyloxycarbonyl-L-phenylalanyl)-amino-4-oxa-1-azabicyclo[3,2,0]heptan-7-one;
(5R,6S)-6-{N-(3-phenylpropionoyl)-L-phenylalanyl}-amino-3-phenyl-4-oxa-1-azabicyclo[3,2,0]heptan-7-one; and
(5S,6S)-6-{N-(3-phenylpropionoyl)-L-phenylalanyl}-amino-3-bromo methyl-4-oxa-1-azabicyclo[3,2,0]heptan-7-one.

6. A pharmaceutical composition, comprising a compound of claim 1 in combination with a pharmaceutically acceptable carrier or diluent.

7. The pharmaceutical composition of claim 6, wherein the pharmaceutical composition is an oral pharmaceutical composition, and the compound is present in the pharmaceutical composition in an amount of about 1 to 25 w/w%.

8. The pharmaceutical composition of claim 6, wherein the pharmaceutical composition is a parenteral pharmaceutical composition, and the compound is present in the pharmaceutical composition in an amount of about 0.1 to 5 w/w%.

9. The pharmaceutical composition of claim 6, wherein the pharmaceutical composition is a topical pharmaceutical composition, and the compound is present in the pharmaceutical composition in an amount of about 1 to 10 w/w%.

10. The compound of claim 1, wherein the amino acids are selected from the group consisting of glycine, D- or L-alanine, D- or L-valine, D- or L- leucine, D- or L-isoleucine, D- or L-serine, D- or L-threonine, D- or L-aspartic acid, D- or L-glutamic acid, D- or L-asparagine, D- or L-glutamine, D- or L-lysine, D- or L-arginine, D- or L-phenylalanine, D- or L-tyrosine, D- or L-methionine and D- or L-proline.

11. The compound of claim 1, wherein each of the mono-, bi-, or tricyclic 5–14 membered heterocyclic rings is independently selected from the group consisting of 1,2,3-triazole, 1,2,4-triazole, imidazole, pyrrole, pyrazole, thiophene, pyrrolidine, pyridine, piperidine, pyrimidine, piperazine, morpholine, thiomorpholine, 1-quinoline, 2-quinoline, isoalloxazine, phenoxazine and phenothiazine.

* * * * *

UNITED STATES PATENT AND TRADEMARK OFFICE
CERTIFICATE OF CORRECTION

PATENT NO. : 5,905,076  
DATED : May 18, 1999  
INVENTOR(S) : Singh et al.

Page 1 of 2

It is certified that error appears in the above-identified patent and that said Letters Patent is hereby corrected as shown below:

Column 4, Line 12, please delete " (5R,6S)-6-(N-benzyloxycarbonyl-L-pronyl)-amino-4-oxa- " and insert therefor, -- (5R,6S)-6-(N-benzyloxycarbonyl-L-prolyl)-amino-4-oxa- --

Column 4, Line 43, please delete " proteaess " and insert therefor, -- proteases --

Column 8, Lines 7,40,and 56, please delete "d" and insert therefor, -- δ --

Column 9, Lines 5 and 63, please delete "d" and insert therefor, -- δ --

Column 10, Lines 12 and 29, please delete "d" and insert therefor, -- δ --

Column 11, Line 10, please delete "A mixture of ($^3$S,4S)-3-(N-benzyloxycarbonyl-L-" and insert therefor, -- A mixture of (3S,4S)-3-(N-benzyloxycarbonyl-L- --

Column 11, Line 20, please delete "d" and insert therefor,-- δ --

Column 11, Line 40, please delete "1H NMR (CDC13), d (ppm): 0 (6H,s), 0.85 (9H, s),2.92" and insert therefor,-- 1H NMR (CDCl$_3$), δ (ppm): 0 (6H,s), 0.85 (9H, s),2.92 --

Column 11, Line 48, please delete "deproteced", and insert therefor, -- deprotected --

Column 12, Lines 1,21,and 36, please delete "d", and insert therefor -- δ --

Column 12, Line 52, please delete "$^1$H NMR (CDC13), d (ppm): 2.30 -2.45 (5H, m)," and insert therefor -- $^1$H NMR (CDCl$_3$), δ (ppm): 2.30 -2.45 (5H, m), --

Column 13, Lines 12 and 52, please delete "d" and insert therefor, -- δ --

UNITED STATES PATENT AND TRADEMARK OFFICE
CERTIFICATE OF CORRECTION

PATENT NO. : 5,905,076

DATED : May 18, 1999

INVENTOR(S) : Singh et al.

It is certified that error appears in the above-identified patent and that said Letters Patent is hereby corrected as shown below:

Column 13, Line 37, please delete "$^1$H NMR (CDC13), d (ppm): 2.35-2.55 (2H, m)," and insert therefor, -- $^1$H NMR (CDC1$_3$), δ (ppm): 2.35-2.55 (2H, m), --

Signed and Sealed this

Sixth Day of June, 2000

*Attest:*

Q. TODD DICKINSON

*Attesting Officer*     *Director of Patents and Trademarks*